(12) United States Patent
Pastore et al.

(10) Patent No.: US 10,185,807 B2
(45) Date of Patent: Jan. 22, 2019

(54) SYSTEM AND METHOD FOR CONDUCTING REAL TIME ACTIVE SURVEILLANCE OF DISEASE OUTBREAK

(71) Applicant: MasterCard International Incorporated, Purchase, NY (US)

(72) Inventors: Jeremy Pastore, Brooklyn, NY (US); Michael Zhao, New York, NY (US); Arun Elangovan, Astoria, NY (US)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 1101 days.

(21) Appl. No.: 14/546,634

(22) Filed: Nov. 18, 2014

(65) Prior Publication Data
US 2016/0140311 A1   May 19, 2016

(51) Int. Cl.
   G16H 50/50   (2018.01)
   G06F 19/00   (2018.01)
   G06Q 30/02   (2012.01)

(52) U.S. Cl.
   CPC ..... *G06F 19/3437* (2013.01); *G06Q 30/0201* (2013.01); *G16H 50/50* (2018.01)

(58) Field of Classification Search
   CPC ..... G06Q 50/22–50/24; G06Q 30/0201; G06F 19/30; G06F 19/3437; G16H 50/00; G16H 50/50
   See application file for complete search history.

(56) References Cited

U.S. PATENT DOCUMENTS

| | | | | |
|---|---|---|---|---|
| 7,770,224 B2 * | 8/2010 | Pellegrino | ............... | G08B 31/00 726/23 |
| 2002/0193967 A1 * | 12/2002 | Siegel | .................... | G06Q 50/22 702/187 |
| 2003/0009239 A1 * | 1/2003 | Lombardo | ............. | G16H 10/60 700/30 |
| 2003/0163416 A1 * | 8/2003 | Kitajima | ................ | G06Q 20/02 705/39 |
| 2004/0073459 A1 * | 4/2004 | Barthell | ............. | G06F 19/3493 705/2 |
| 2004/0128184 A1 * | 7/2004 | Bracken | ................ | G06F 19/328 705/7.34 |
| 2005/0055330 A1 * | 3/2005 | Britton | .................... | H04L 67/42 |
| 2009/0216747 A1 * | 8/2009 | Li | ........................ | G06Q 10/067 |

(Continued)

*Primary Examiner* — Robert A Sorey
(74) *Attorney, Agent, or Firm* — Leason Ellis LLP (57) ABSTRACT

A system and method is disclosed for the real-time active surveillance of disease. The system generates an outbreak detection model by analyzing the spending records of individuals who are known to be infected to identify purchases and purchase patterns that correlate to infection in the population with a disease. Based on the identified purchases, the system generates probabilistic identification criteria and merges the criteria to simulation models of infection spread by geography to generate a geospatial outbreak detection model. The system applies the generated model to spending records, in real time, to identify and monitor disease spread in the population. The system can also generate alerts if the likelihood that an individual is infected, or one or more individuals in a set or population is infected exceeds a threshold. Actions are taken at remote devices, such as mobile phones, computers and POS terminals in certain embodiments.

21 Claims, 4 Drawing Sheets

(56) References Cited

U.S. PATENT DOCUMENTS

| | | | | |
|---|---|---|---|---|
| 2010/0021937 A1* | 1/2010 | Greenberg | ............ | G01N 33/569 |
| | | | | 435/7.2 |
| 2010/0332403 A1* | 12/2010 | Angell | .................... | G06Q 10/30 |
| | | | | 705/308 |
| 2011/0125529 A1* | 5/2011 | Miller | ................. | G06F 19/3456 |
| | | | | 705/3 |
| 2011/0173045 A1* | 7/2011 | Jaine | ...................... | G06Q 10/06 |
| | | | | 705/7.28 |
| 2012/0150562 A1* | 6/2012 | Lerner | ................... | G06Q 50/22 |
| | | | | 705/3 |
| 2012/0310410 A1* | 12/2012 | Adams | ...................... | E05G 1/04 |
| | | | | 700/237 |
| 2013/0304486 A1* | 11/2013 | Jagemann | .......... | G06Q 30/0603 |
| | | | | 705/2 |
| 2014/0095417 A1* | 4/2014 | Herz | ................... | G06N 99/005 |
| | | | | 706/12 |
| 2015/0242586 A1* | 8/2015 | Kagen | ................ | G06F 19/3431 |
| | | | | 705/2 |
| 2015/0337388 A1* | 11/2015 | Garner, Jr. | ........... | C12Q 1/6886 |
| | | | | 506/8 |
| 2016/0314256 A1* | 10/2016 | Su | ........................ | G06F 19/345 |

* cited by examiner

SYSTEM AND METHOD FOR CONDUCTING REAL TIME ACTIVE SURVEILLANCE OF DISEASE OUTBREAK

TECHNICAL FIELD OF THE DISCLOSURE

This patent application relates generally to the field of monitoring disease outbreaks, and more particularly to detecting and monitoring disease outbreaks based on purchase data.

BACKGROUND OF THE DISCLOSURE

Disease surveillance is a practice by which the spread of disease is monitored in order to predict, observe, and minimize the harm caused by outbreak, epidemic, and pandemic situations. Most existing disease detection and monitoring systems rely on voluntary reporting of medical conditions by infected individuals or healthcare providers. Based on the information the monitoring bodies can observe and model the spread of the diseases.

Because the traditional approach to disease surveillance relies on voluntary participation, the information received is often incomplete. For example, many individuals fail to report infection. The individuals that do report are often unable to provide a complete description of their symptoms and activity leading up to and even after the diagnosis. Accordingly, this practice provides a limited sample of information that is often inadequate for effectively detecting and monitoring the spread of a disease. In addition, existing methods for predicting disease outbreak or monitoring infection spread often cannot effectively determine the current state of infection spread because information about infected individuals is generally received only after the individuals have been diagnosed and the condition is reported to the monitoring body. Such latencies make it difficult to preemptively warn individuals in high risk populations, and take preventative measures, especially when the infection is a rapidly spreading through the population.

People commonly conduct electronic transactions as they go about their daily lives, for example, using credit and debit cards to purchase goods and services from merchants and service providers. When conducting electronic transactions, either at a brick and mortar location or via the internet, the information concerning the transaction is collected and stored in one or more databases including the account holder's information, the location of the purchase, the time of the purchase and purchase data (e.g., purchase details), for instance, a merchant name, a type of merchant, product/service purchased and other such information regarding the transaction. The payment database of spending records is continuously updating in real time or near real time as consumers continue to make electronic purchases. Accordingly, payment transactions provide a continuously updating source of information from which disease outbreak in individuals, groups and populations can be detected and monitored and otherwise surveyed.

Accordingly, it is desirable for a system and method for accurately detecting and monitoring infection spread from a database of spending records and without reliance on individuals to actively volunteer information. Furthermore, it is desirable for a system that can detect and monitor disease spread in real time or near-real time. It should be apparent that, depending on applicable laws and regulations, a consumer can opt in, thereby consenting to the use of their payment records as well as any other personal information he or she provides to the systems for active surveillance of disease outbreak.

It is with respect to these and other considerations that the disclosure made herein is presented.

SUMMARY OF CERTAIN EMBODIMENTS OF THE DISCLOSURE

According to a first aspect, a computer implemented method is provided for real-time active surveillance of disease outbreak in a population of individuals. The method detects and monitors disease outbreak from a database of spending records that includes SKU-level data, including temporal data, geographic data and other details concerning purchases conducted by individuals in the population. The database of spending records is updated in real time as the individuals conduct additional purchases. The method includes, providing the identity of individuals from among the population who are known to be infected by at least one disease ("infected individuals") and accessing respective spending records for each of the infected individuals from the database.

The method includes identifying, from the respective spending records, purchases that are indicative of infection in the population with the at least one disease. The step of identifying purchases that are indicative of infection in the population can include analyzing the respective spending records and correlating the respective purchases with indicia of infection associated with the at least one disease. The correlation can be based on the SKU-level data, including temporal data and geographic data and purchase data concerning the respective purchases. The method also includes determining probabilistic identification criteria based on the correlation of the respective purchases with the indicia of infection. The method also includes generating a geospatial outbreak detection model based on the probabilistic identification criteria and at least one simulation model of infection spread by geography. The geospatial outbreak detection model is generated by seeding the at least one simulation model using the geographic data and temporal data included in the respective spending records for the infected individuals. The method also includes applying the geospatial outbreak detection model to the database of spending records, in real-time to identify one or more other purchases that are indicative of infection in the population. The one or more other purchases are conducted by one or more other individuals from among the population who are not known to be infected by the at least one disease ("candidate individuals"). The method also includes calculating the likelihood that one or more of the candidate individuals are infected based on the one or more other purchases and the probabilistic identification criteria and generating an alert if the calculated likelihood exceeds a threshold likelihood.

According to another aspect, a system is provided for real-time active surveillance of disease outbreak in a population of individuals from a database of spending records that is updated in real time as the individuals conduct additional purchases. The spending records can include SKU-level data, including temporal data and graphic data and purchase data concerning purchases made by individuals in the population. The system comprises a processor configured to interact with a computer-readable storage medium and execute instructions in the form of one or more software modules stored on the storage medium. The software modules include a database module that configures the processor to access, from the database, respective spending records for each of a plurality of individuals from among the population who were previously identified as being infected by at least one disease ("infected individuals").

The software modules also includes an analysis module, that configures the processor to: 1) identify from the respective spending records, purchases that are indicative of infection in the population with the at least one disease by analyzing the respective spending records, and correlating the respective purchases with indicia of infection associated with the at least one disease based on the SKU-level data, including the temporal data and/or the geographic data and purchase data concerning the respective purchases; 2) determine probabilistic identification criteria based on the correlation of the respective purchases with the indicia of infection; 3) apply a geospatial outbreak detection model to the database of spending records, in real-time, to identify one or more other purchases that are indicative of infection in the population, wherein the one or more other purchases are conducted by one or more other individuals from among the population who are not known to be infected by the at least one disease ("candidate individuals"); and 4) calculate a likelihood that one or more of the candidate individuals are infected based on the one or more other purchases and the probabilistic identification criteria.

The software modules also include a modeling module that configures the processor to generate the geospatial outbreak detection model as a function of the probabilistic identification criteria and at least one simulation model of infection spread by geography. The geospatial outbreak detection model is generated by seeding the at least one simulation model using the geographic data and temporal data included in the respective spending records for the infected individuals. The software modules also include a reporting module that configures the processor to generate an alert if the calculated likelihood exceeds a threshold likelihood.

These and other aspects, features, and advantages can be appreciated from the accompanying description of certain embodiments of the disclosure and the accompanying drawing figures and claims.

DETAILED DESCRIPTION OF CERTAIN EMBODIMENTS OF THE DISCLOSURE

By way of overview and introduction, various systems and methods are described herein that facilitate and enable the real-time active surveillance of disease. The systems and methods have the end goal of detecting and monitoring the spread of diseases through a population of people. The system can achieve this through a two stage process, developing an outbreak detection model and then applying the model to purchasing data, as it is collected in real time, to monitor the spread of disease. The modeling process includes, analyzing, by the system using a database of spending records, the spending records of individuals who are known to be infected "infected individuals" in order to identify purchases and purchasing patterns that are indicative of infection in the population with the disease. More specifically, the system can identify purchases and purchasing patterns that are common to infected individuals (as compared to non-infected individuals) and accordingly exhibit a correlation to infection in the population with the disease. The system can also compare the spending records to known indicia of infection to correlate purchases with infection by the disease. In addition, the system can determine probabilistic identification criteria based on how strongly purchases and purchasing patterns correlate to infection by the disease. The probabilistic identification criteria can then be applied to a simulation model of infection spread by geography to generate a geospatial outbreak detection model.

The second stage of the active disease outbreak surveillance process involves applying the geospatial outbreak detection model to the database of spending records as it is updated in real time. More specifically, the spending records that are stored to the database in real time are compared to the probabilistic identification criteria to identify whether one or more additional people exhibit signs of infection by a disease and to determine a likelihood that the one or more additional people are infected. If the likelihood exceeds a threshold, the system can generate an alert that is transmitted to individuals in the population and/or to disease control organizations/authorities.

The following detailed description is directed to systems and methods for real-time active surveillance of disease outbreak. The referenced systems and methods are now described more fully with reference to the accompanying drawings, in which one or more illustrated embodiments and/or arrangements of the systems and methods are shown. The systems and methods are not limited in any way to the illustrated embodiments and/or arrangements as the illustrated embodiments and/or arrangements described below are merely exemplary of the systems and methods, which can be embodied in various forms, as appreciated by one skilled in the art. Therefore, it is to be understood that any structural and functional details disclosed herein are not to be interpreted as limiting the systems and methods, but rather, are provided as a representative embodiment and/or arrangement for teaching one skilled in the art one or more ways to implement the systems and methods. Accordingly, aspects of the present systems and methods can take the form of an entirely hardware embodiment, an entirely software embodiment (including firmware, resident software, micro-code, etc.), or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer. Furthermore, the terms and phrases used herein are not intended to be limiting, but rather, are to provide an understandable description of the systems and methods.

Figure 1:
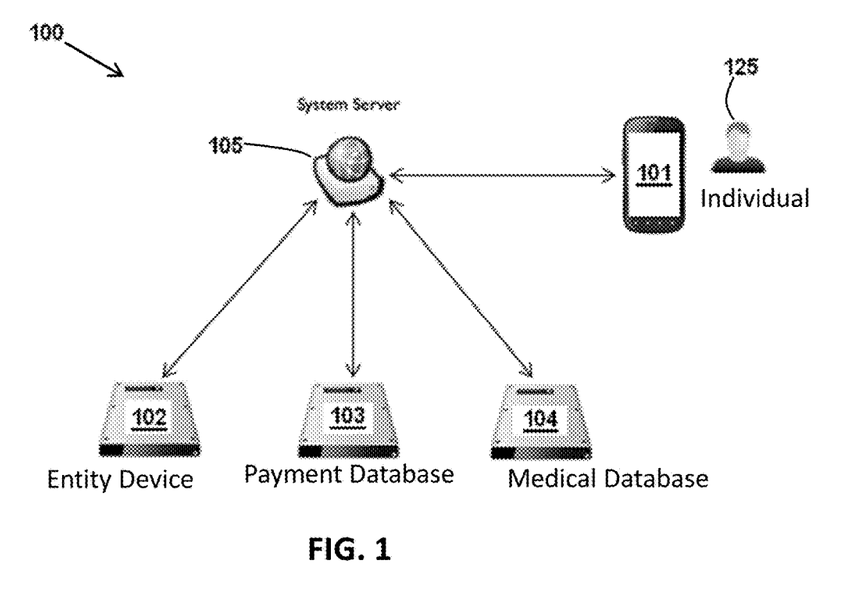
FIG. 1 is a high-level diagram illustrating an exemplary configuration of a system for conducting real-time active surveillance of disease outbreak in accordance with at least one embodiment disclosed herein.

An exemplary system is shown as a block diagram in FIG. 1 which is a high-level diagram illustrating an exemplary configuration of the system for conducting real-time active surveillance of disease outbreak 100. In one arrangement, the system 100 consists of a system server 105 communicatively coupled to at least one payment database 103 and one or more remote computing devices. The remote computing devices (e.g., individual device 101, and entity device 102) can be associated with individuals (e.g., individual 125) from among the population and/or other medical and regulatory entities such as the Center For Disease Control and Prevention (CDC). In addition, the system server 105 can also be communicatively coupled to a medical database 104 that is configured to store medical data for a plurality of individuals in the population.

The system server 105 can be practically any computing device and/or data processing apparatus capable of communicating with remote computing devices, data storage devices and computing networks (e.g., individual device 101, entity device 102, payment database 103, medical database 104, and the like), receiving, transmitting and storing electronic information and processing information as further described herein. Similarly, payment database 103 and medical database 104 are intended to represent various forms of digital computers, such as laptops, desktops, workstations, servers, blade servers, mainframes, and other appropriate computers and/or networked or cloud based computing systems.

Remote computing devices, e.g., individual device 101 and entity device 102, can be configured to collect (and/or display) information from one or more individuals in the population and entities, communicate the information to the system server 105 and receive information from the system server. It should be understood that remote computing devices can be any computing device and/or data processing apparatus capable of embodying the systems and/or methods described herein, including, but not limited to, a personal computer, tablet computer or smart phone device.

Embodiments of the methods and systems described herein, in particular, the payment database 103, can be associated with a payment processing subsystem that is configured to record and/or process spending records detailing purchase transactions conducted by consumers (e.g., individual 125) and one or more merchants or service providers. For example and without limitation, payment database 103 can be associated with a payment card network operated by MasterCard International Incorporated of Purchase N.Y., the assignee of the present disclosure.

Accordingly, payment database 103 can store information spending records concerning purchase transactions performed by individuals in the population with merchants using a transaction card. As used herein, the terms "transaction card," "financial transaction card," and "payment card" refer to any suitable transaction card, such as a credit card, a debit card, a prepaid card, a charge card, a membership card, a promotional card, a frequent flyer card, an identification card, a prepaid card, a gift card, and/or any other device that may hold payment account information, such as mobile phones, smartphones, personal digital assistants (PDAs), digital wallets, key fobs, and/or computers and cloud-based payment schemes. Each type of transaction card can be used as a method of payment for performing a transaction. As would be understood by those skilled in the art, after a purchase has been made using a transaction card, a clearing process occurs to transfer additional transaction data related to the purchase among the parties to the transaction, such as a merchant bank, an interchange network, and issuer bank. More specifically, during and/or after the clearing process, SKU-level data, such as a time of purchase, geographic location of purchase, and purchase data including: a merchant name, a type of merchant, cardholder account information, a type of transaction, information regarding the purchased item and/or service, and/or other suitable information associated with a transaction can be transmitted between parties to the transaction and may be stored by any of the parties to the transaction, for example, in payment database 103.

Figure 2:
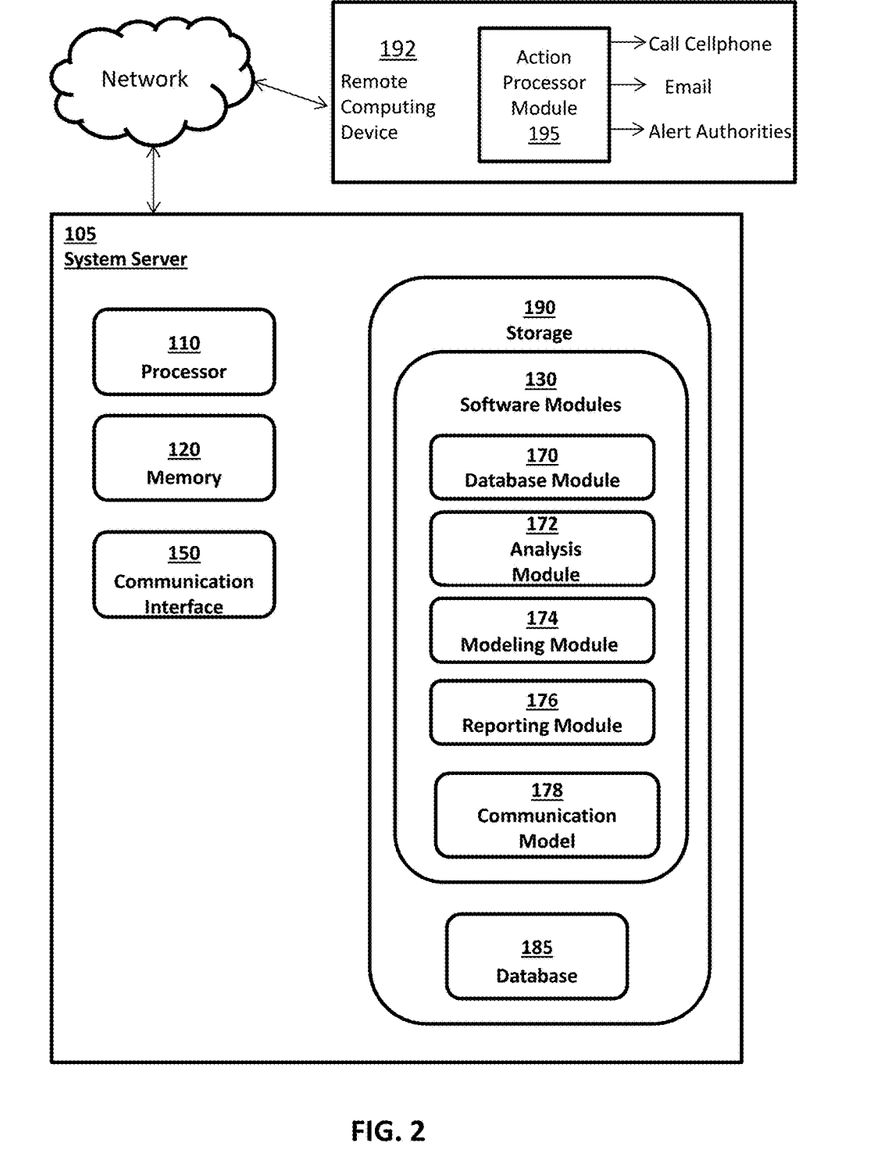
FIG. 2 is a block diagram illustrating an exemplary configuration of a system for conducting real-time active surveillance of disease outbreak in accordance with at least one embodiment disclosed herein.

In reference to FIG. 2, system server 105 of the system for conducting real-time active surveillance of disease outbreak 100 is arranged with various hardware and software components that serve to enable operation of the system, including a processor 110, a memory 120, a storage 190 and a communication interface 150. The processor 110 serves to execute software instructions that can be loaded into the memory 120. The processor 110 can be a number of processors, a multi-processor core, or some other type of processor, depending on the particular implementation.

Preferably, the memory 120 and/or the storage 190 are accessible by the processor 110, thereby enabling the processor 110 to receive and execute instructions stored on the memory 120 and/or on the storage 190. The memory 120 can be, for example, a random access memory (RAM) or any other suitable volatile or non-volatile computer readable storage medium. In addition, the memory 120 can be fixed or removable. The storage 190 can take various forms, depending on the particular implementation. For example, the storage 190 can contain one or more components or devices such as a hard drive, a flash memory, a rewritable optical disk, a rewritable magnetic tape, or some combination of the above. The storage 190 also can be fixed or removable or remote such as cloud based data storage systems.

The one or more software modules 130 are encoded in the storage 190 and/or in the memory 120. The software modules 130 can comprise one or more software programs or applications having computer program code or a set of instructions executed in the processor 110. Such computer program code or instructions for carrying out operations for aspects of the systems and methods disclosed herein can be written in any combination of one or more programming languages. The program code can execute entirely on system server 105, partly on system server 105, as a stand-alone software package, partly on system server 105 and partly on a remote computer/device such as individual device 101, entity device 102, or any computing devices maintaining the payment database 103 or the medical database 104 or entirely on the remote computers/devices. In the latter scenario, the remote computer systems can be connected to system server 105 through any type of network, including a local area network (LAN) or a wide area network (WAN), or the connection can be made to an external computer (for example, through the Internet using an Internet Service Provider).

Preferably, included among the software modules 130 is a database module 170, an analysis module 172, a modeling module 174, a reporting module 176 and a communication module 178, that are executed by processor 110. During execution of the software modules 130, the processor 110 is configured to perform various operations relating to the real-time active surveillance of disease outbreak, as will be described in greater detail below.

It can also be said that the program code of the software modules 130 and one or more of the non-transitory computer readable storage devices (such as the memory 120 and/or the storage 190) form a computer program product that can be manufactured and/or distributed in accordance with the present disclosure, as is known to those of ordinary skill in the art.

It should be understood that in some illustrative embodiments, one or more of the software modules 130 can be downloaded over a network to the storage 190 from another device or system via communication interface 150 for use within the system for conducting real-time active surveillance of disease outbreak 100. In addition, it should be noted that other information and/or data relevant to the operation of the present systems and methods can also be stored on the storage 190, as will be discussed in greater detail below.

A database 185 can also be stored on the storage 190. Database 185 can contain and/or maintain various data items and elements that are utilized throughout the various operations of the system for conducting real-time active surveillance of disease outbreak 100. The information stored in database 185 can include, but is not limited to, information relating to one or more diseases, spending records, and demographic data relating to the individuals in the population, as will be described in greater detail herein. It should be noted that although database 185 is depicted as being configured locally to system server 105, in certain implementations, database 185 and/or various of the data elements stored therein can be located remotely (such as on a remote device or server—not shown) and connected to system server 105 through a network in a manner known to those of ordinary skill in the art.

A communication interface 150 is also operatively connected to the processor 110 and can be any interface that enables communication between the system server 105 and external devices, machines and/or elements. Preferably, the communication interface 150 includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting system server 105 to other computing devices and/or communication networks, such as private networks and the Internet. Such connections can include a wired connection or a wireless connection (e.g., using the IEEE 802.11 standard) though it should be understood that communication interface 150 can be practically any interface that enables communication to/from the system server 105.

It should be understood that any of the computing devices 101, 102, 103, 104 can be in direct communication with system server 105, indirect communication with system server 105, and/or can be communicatively coordinated with system server 105 through a computer network such as the Internet.

The operation of the system for real-time active surveillance of disease outbreak 100 and the various elements and components described above will be further appreciated with reference to the method for real-time active surveillance of disease outbreak as described below, in conjunction with FIG. 3.

At some point prior to conducting real-time active surveillance of disease outbreak in accordance with at least one embodiment disclosed herein, one or more of the individuals in the population can be enrolled to participate in the program for real-time active surveillance of disease outbreak implemented by the system. For example, this can be done by connecting to system server 105 using a consumer device 101 and actively providing personal information, such as, payment account information and/or medical information and the like. It should be understood that, alternatively, the individuals can simply opt in by providing a few key pieces of personal information, such as a name and/or social security number, and grant permission for the system server 105 to access his or her spending records and/or medical data from the appropriate data storage devices (e.g., payment database 103 or medical database 104). In addition, the particular consumer's information could be automatically available to the system by virtue of having a payment card issued by a participating card issuer. In addition, a consumer can be automatically enrolled from using a particular medical provider, medical insurance program and the like. Using either personal information or payment information, system server 105, via a transaction processing company, card issuer, and the like, can automatically retrieve spending records for the particular consumer. Any automatic access to a consumer's spending records or medical information would be subject to applicable data privacy and data usages laws.

It should be understood that spending records and/or medical data can be provided by the consumer or also received directly from a participating medical service provider company, with the appropriate consents from the consumer. It should also be understood that the consumer can also require authorization before the system server retrieves spending records and/or medical information. Thus, it should be apparent that in the exemplary system and routine described herein, depending on applicable laws and regulations, a consumer can opt in, thereby consenting to the use of their spending records as well as any other personal information he or she provides.

For situations in which the systems discussed here collect personal information about individuals, the individuals may be provided with an opportunity to control the manner such information is collected with respect to programs or features that may collect personal information (e.g., information about an individual's medical data, spending records or an individual's current location/address). Individuals may also be informed of the accompanying limitations on the functionality of a service that may result from limiting access to such personal information. In addition, certain data may be anonymized in one or more ways before it is stored or used, so that personally identifiable information is removed. For example, identifiers associated with an individual's identity, payment records and/or medical records may be anonymized so that no personally identifiable information can be determined for the individuals.

Figure 3:
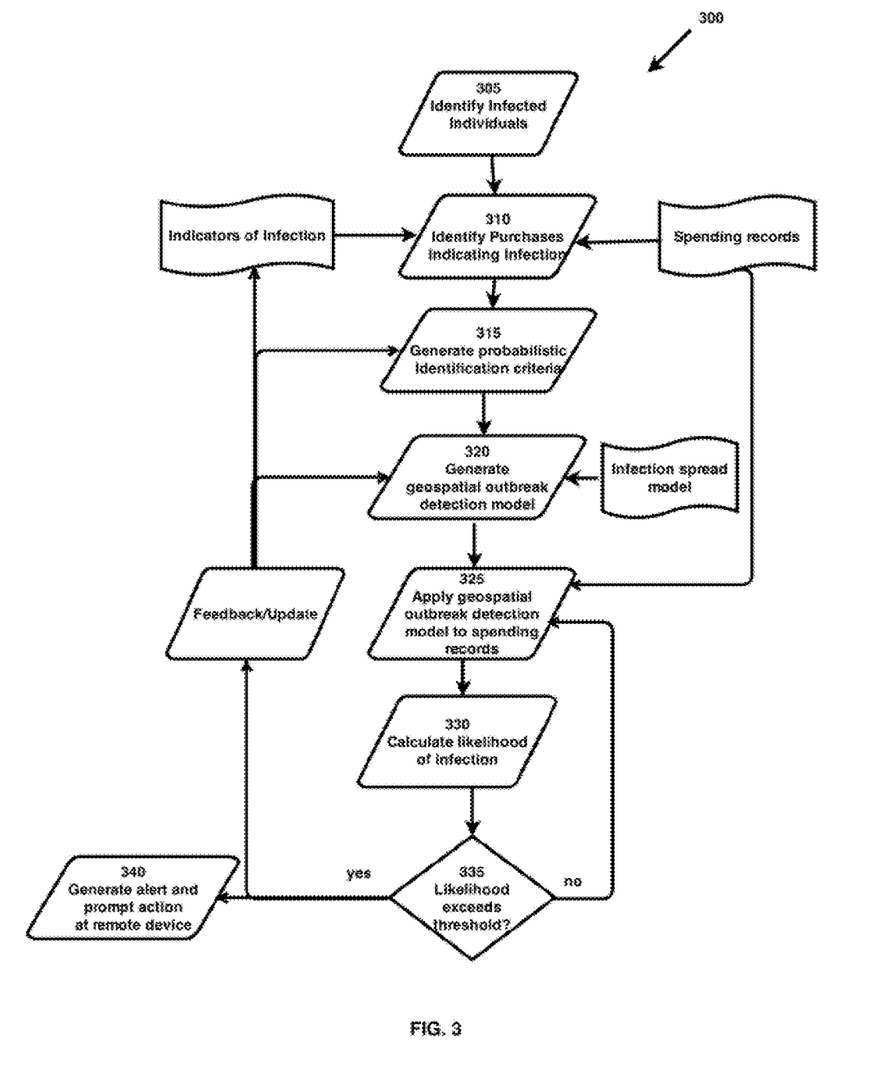
FIG. 3 is a flow diagram illustrating a routine for conducting real-time active surveillance of disease outbreak in accordance with at least one embodiment disclosed herein.

Turning now to FIG. 3, a flow diagram illustrates a routine 300 for conducting real-time active surveillance of disease outbreak in accordance with at least one embodiment disclosed herein. The process begins at step 305, in which the identity of individuals from among the population who are known to be infected by a disease ("infected individuals") is provided to the system server 105. As noted above, the "identity" of infected individuals can be anonymized so that no personally identifiable information can be determined for the individuals. In some implementations, the infected individuals can be identified from an external source of such information. For example, the processor 110, which is configured by executing one or more of the software modules 130, including, preferably, the database module 170, the analysis module 172, and the communication module 178, can query a medical database 104 for the identity of one or more infected individuals. In addition or alternatively, the identity of the infected individuals can also be actively provided to the system server 105. For example, by the infected individuals themselves, or by an entity that monitors disease outbreak, e.g., the CDC, using consumer device 101 or entity device 102, respectively.

Once a sample set of infected individuals are identified, then, at step 310, the system analyzes the payment records of the infected individuals to identify purchases that are indicative of infection in the population by the disease. More particularly, by example and without limitation, the processor 110, which is configured by executing one or more of the software modules 130, including, preferably, the database module 170, the analysis module 172, and the communication module 176, can access the payment database 103 for the payment records associated with respective infected individuals.

It should also be understood that the spending records and/or medical data, which is further described herein, can be retrieved prior to detecting and monitoring disease spread, dynamically when detecting and monitoring disease spread or a combination of the foregoing.

Spending records can include, but are not limited to, the particular consumer's transaction history using a variety of payment methods, such as a credit card, a debit card, a prepaid card, a gift card, bank account bill-pay service, ACH payment, a TSM account, or a combination of the foregoing. The spending records can be retrieved from a first data source, such as payment database 103, which can be operated by a payment service provider, such as MasterCard International Incorporated, the assignee of the present disclosure.

The configured processor 110 can then analyze the SKU-level data included in the payment records to identify purchases made by the infected individuals that are indicative of infection in the population with the at least one disease. As noted above, SKU-level data identifies one or more of a product, a service, a merchant, a location of purchase, a time of purchase and other such information that describes the purchase transaction made by the infected individuals.

In some implementations, the SKU-level data can be compared to indicators of infection and a correlation between the purchase and one or more of the indicators can be determined. Indicators of infection are purchase attributes that are known to be associated with infection by the at least one disease. For example, and without limitation, the indicators can range from broad categories (e.g., vitamins or health food stores) to specific products or merchants/service providers (e.g., a particular pharmaceutical product, vitamin, or medical provider) that have been associated with the infection or otherwise relate to infection with the disease. Indicators of infection can also be attributes that represent risk factors associated with infection by the disease, for example, a particular location and/or a time and date that has also been associated with the infection. For example, a location and date/time that an infected individual was at a particular place can represent a heightened risk of infection for other individuals having been at that particular place and time/date.

It can be appreciated that certain indicators of infection can have stronger relation to a particular disease than others and the indicators can be weighted accordingly. For example, a purchase of vitamin C might not relate as strongly to a disease than a specific drug that is a known treatment for a particular infection. In addition, how closely a purchase correlates to the one or more known indicators can also vary. For example, certain purchases might match a particular indicator exactly, whereas other purchases have a weaker correlation. Accordingly, the purchase data-points can be weighted according to the strength of the correlation.

Identifying purchases that are indicative of infection with the at least one disease can also include identifying purchasing patterns or habits that are indicative of infection with the at least one disease. More specifically, the configured processor 110 can compare the purchases of two or more of the infected individuals to identify similarities between their respective purchases. The analysis can be based on the SKU-level data, including the temporal data and the geographic data and purchase data associated with the purchases, and can be performed using any number of mathematical analysis techniques, including principal component analysis (PCA) and other such statistical tools, as would be understood by those in the art. In this manner, purchasing patterns and the habits of infected individuals that are indicative of infection can be identified based on the SKU-level purchase data, including geographic data, temporal data and purchase data for example, to identify physical/temporal intersections as well as similarities in the products/services purchased by infected individuals.

It can be appreciated that spending records can be analyzed and correlated to infection with the at least one disease on an individual level. It can also be appreciated that spending records for sets of individuals and larger populations of individuals can be analyzed to identify purchasing patterns, habits and trends exhibited by the sets and/or population that are indicative of the presence of one or more individuals who are infected by the at least one disease.

It should be understood that the system can segment the data being analyzed or the results according to segmentation data, such as demographic data relating to the individuals in the population that can include, but is not limited to, the particular individual's age, address, location, education level, occupation, and family-related data, such as marital status and number of children and the like. Demographic data can be determined by analyzing the spending records retrieved from the payment database 103 or medical data retrieved from the medical database 104. It should also be understood that demographic data can be obtained from third party providers of such information or from the individuals themselves.

Then at step 315, probabilistic identification criteria are determined based on the correlation of purchases to the indicators of infection. Probabilistic identification criteria represent the probability that certain purchases and/or purchase patterns are indicative of infection in the population by a particular disease. The criteria are usable to identify individuals from among the population that are potentially infected by the at least one disease ("candidate individuals") from their purchase records. Similarly, the probabilistic identification criteria are usable to determine whether sets of individuals, or populations, exhibit signs of infection by the at least one disease. For example, these higher level probabilistic identification criteria that represent purchasing trends exhibited by sets or populations of individuals that include one or more infected individuals and are associated with a respective probability that the characterized trend is indicative of infection in the set/population.

More specifically, the processor 110, which is configured by executing one or more of the software modules 130, including, preferably, the database module 170, the analysis module 172, the modeling module 174 can apply an algorithm that, based on the strength of the correlation between the purchase(s) and the indicator(s), and based on how strongly the one or more indicators relate to infection by the disease, assigns probabilistic values that take into account these variations.

In addition, the configured processor can generate criteria (e.g., assertions) that can be applied to the payment records by generalizing various details of the purchases and/or purchasing patterns that indicate infection. In some implementations, this process generating the assertions can include isolating geographic aspects, temporal aspects and/or other SKU-level features of the purchases (or purchase patterns) that are determined to be relevant to infection and discounting or discarding other characteristics of the purchases that are of lesser importance or relevance to infection. For instance, based on an infected individuals purchase of, say, a stick of gum, at a particular location at a particular time, the configured processor can generate a probabilistic identification criteria that identifies the particular location and time as a risk factor but without limiting the criteria to the particular item purchased. Accordingly, as further described herein, purchases made by candidate individuals at that particular location and around that time can be matched to the probabilistic identification criteria and flagged as indicating possible infection of the candidate individuals, without requiring those candidate individuals to purchase a stick of gum to satisfy the identification criteria.

Generating identification criteria can also include analyzing the purchases and/or purchasing patterns and extrapolating set level or population level observations so as to generate assertions that can be applied to set level and population level spending records, instead of on an individual consumer basis.

It can be appreciated that the probabilistic identification criteria can also be used as feedback to update and supplement the known indicators of infection. Accordingly, the configured processor can, based on how closely the criteria are linked to the infection, add the identification criteria to the known set of indicators of infection so as to provide a more complete and dynamically updating set of indicators as more data is being analyzed and more purchases and patterns are determined to relate to infection with the disease.

It can be appreciated that the probabilistic identification criteria and indicators of infection can be used as a model to identify, by the configured processor 110 using the database of payment data 103, other potentially infected individuals ("candidate individuals") or identify set and population level purchase trends that are indicative of infection within the set or population. However, as further described herein, the probabilistic identification criteria can be combined with other models, for instance, geographic and temporal infection spread models, to generate more complex and refined models for identifying and monitoring infection spread.

At step 320, the processor 110 executing one or more of the software modules 130, including, preferably, the database module 170, the analysis module 172, and the modeling module 174, can merge the probabilistic identification criteria with one or more simulation models of infection spread by geography.

As would be understood by those skilled in the art, there exist algorithmic models that project how various diseases spread through a population. Because infection with disease is commonly spread through human-human interaction, such geographic infection spread models are used to project the spread of diseases within a population across a geographic area and over time. The geographic spread model used can be specific to a particular disease, for example, a model for the spread of influenza based on previous influenza outbreaks. In addition or alternatively, the particular spread model can be based on the spread of one or more other diseases that are selected to approximate the spread of the at least one disease based on common characteristics, for example, geographic spread rate and the like.

Moreover, the configured processor 110 can input SKU-level data from the payment records, including the time and/or location of one or more purchases made by the known infected individuals, into the geographic infection spread model to seed the model according to the currently known data about the infected individuals. Accordingly, the seeded model can be used to guide the surveillance disease outbreak based on the probabilistic identification criteria to those geographic areas that are most likely to exhibit infection spread based on the current state of the disease outbreak.

In some implementations, the merged model can be back tested against known infections/epidemics to test and refine the model. For example, the merged model can be applied to historical spending records and compared to the actual spread of infection with a disease through the population during a previous outbreak and the model can be refined based on how closely the model matched the historic outbreak. More specifically, the configured processor can systematically vary the probabilities associated with the probabilistic identification criteria or apply a different geographic spread model and compare the adjusted model to the actual outbreak spread. In addition, the configured processor can systematically adjust the weights associated with the indicia of infection, or refine the algorithmic correlation of purchases and purchase patterns to the indicia of infection to better fit the historic outbreak data.

At step 325, the system identifies and monitors infection spread by applying the geospatial outbreak detection model to the database of spending records. In some implementations, the processor 110 executing one or more of the software modules 130, including, preferably, the database module 170 and the analysis module 172 can apply the apply the geospatial outbreak detection model to the spending records to identify one or more other purchases conducted by one or more other individuals from among the population who are not known to be infected by the at least one disease ("candidate individuals") that are indicative of infection in the population.

The configured processor can apply the geospatial outbreak detection model to the historical spending records that is currently available to the system to identify the current state of infection spread. As further described herein, the geospatial outbreak detection model can be updated based on the current state of infection spread such that the system can more efficiently and accurately monitor infection spread based on new payment records as they are received in near real time and in view of the updated model.

The identification and monitoring of disease spread can be performed at an individual level, the set level and population level. For example, the probabilistic identification criteria that concern individual consumer activity can be compared to payment records for candidate individuals to determine whether the candidate individual's purchases indicate infection. By way of further example, the spending records associated with sets of candidate individuals can be analyzed to identify set level payment trends and compared to the probabilistic identification criteria that concern set-level payment activity to determine whether one or more of the candidate individuals in the set are likely to be infected. Similarly, the probabilistic identification criteria can be applied to population level payment trends.

In addition the configured processor can selectively analyze payment records stored in the payment database according to the geospatial infection spread model. For example, to focus the analysis on transactions performed in one or more geographic locations that are more likely to exhibit infection spread rather than locations that are not as likely to exhibit infection spread. Selective analysis can minimize computing time or achieve other such efficiency goals as would be understood by those skilled in the art.

Moreover, the order in which the spending records is analyzed in view of the probabilistic identification criteria can be prioritized based on various factors. For example and without limitation, spending records can be analyzed as a function of the relative ease with which the spending records can be retrieved and/or algorithmically compared to the probabilistic identification criteria. By way of further example, the payment records can be analyzed based on the probability assigned to the probabilistic identification criteria, so as to consider criteria that concern stronger indicators of infection before the criteria that concern weaker indicators, and vice versa.

In addition or alternatively the payment records can be analyzed at higher levels of abstraction and then the algorithm can drill down to the set level data and then individual level data points. For example, population level purchasing data can be analyzed and, provided the population level purchasing trends are indicative of disease spread, set level purchasing data can be analyzed to identify the presence of infection in subsets of the population Of this limited set of candidate individuals, the system can then perform a further selective review of spending records to determine whether one or more of the candidate individuals are infected by the disease.

By way of further example, the geographic locations identified by the infection spread model as high risk areas can be analyzed with higher scrutiny as compared to lower risk geographic locations. For example, an analysis of individual payment records can be performed on the candidate individuals in the high risk areas and population level trends can be monitored in lower risk areas.

It should be understood that steps for analyzing spending records in view of the generated model can be broken into sub-routines that can be performed in any suitable order or according to any combination of priorities. It should also be understood that the spending records can be analyzed for any number of past time periods, including without limitation, weekly, monthly, quarterly, yearly, etc. by aggregating the spending records for the given time period prior to application of the geospatial outbreak model. In addition or alternatively the system can monitor disease spread in near real time as spending records is received and stored in the payment database.

Application of the geospatial outbreak detection model to the spending records to identify purchases that are indicative of infection in the population can include comparing, by the configured processor 110, the information associated with one or more purchases stored in the payment database to one or more of the probabilistic identification criteria. The comparison can be based on the SKU-level data, including the temporal data and the geographic data associated with the one or more purchases, or any combination of the foregoing. Accordingly, the one or more purchases can be matched based on physical/temporal similarities as well as the products/services purchased. The matching can be performed using any number of algorithmic and mathematical comparison and matching techniques, as would be understood by those in the art. In some implementations, the configured processor 110 can also determine how closely the one or more purchases satisfy the probabilistic identification criteria and a score can be assigned. The score can be assigned on a transaction by transaction basis or can be assigned to the candidate individual's respective spending records on an overall basis. Similarly, a score can be assigned to set or population level purchasing data based on comparison to set and population level probabilistic identification criteria.

It should be understood that the configured processor 110 can similarly analyze and monitor the spending records of known infected individuals and individuals that are identified as likely to be infected to update and refine the geospatial outbreak model. For example, using the historical spending records for these individuals or the spending records received in near-real time, the configured processor can repeat steps 310-325 to refine the set of indicators of infection, the probabilistic identification criteria and the geospatial outbreak detection model, so as to provide a more complete and dynamically updating geospatial outbreak detection model as data is being collected and more individuals are determined be infected with the at least one disease.

At step 330, the processor 110, which is configured by executing one or more of the software modules 130, including, preferably, the analysis module 172, can calculate a likelihood of infection. A calculated likelihood of infection represents how likely it is that a particular individual is infected with the at least one disease, or how likely it is that a set or population of individuals includes one or more individuals who are infected by the at least one disease. The likelihood of infection can be computed based on the probabilities assigned to the probabilistic identification criteria determined to be matched by the one or more payment records. In addition, the likelihood of infection can also be calculated as a function of the score that represents how closely the one or more purchases match the probabilistic identification criteria. In this manner, a probability of infection can be determined for candidate individuals, sets and populations of individuals based on the purchasing data that is analyzed and the probabilistic identification criteria that are applied.

At step 335, candidate individuals, sets of individuals or populations of individuals that are likely to be infected (e.g., exhibiting signs of infection) are identified. More specifically, the processor 110, which is configured by executing one or more of the software modules 130, including, preferably, the analysis module 172 can compare the calculated likelihood to one or more prescribed threshold levels. The threshold level can be pre-set such that such that a candidate individual is positively identified as infected when it is sufficiently likely that the individual is infected by the at least one disease. Threshold levels can also be prescribed so that sets and populations of individuals are identified if it sufficiently likely that a prescribed number of individuals in a particular set or population are likely to be infected.

As shown in FIG. 3, in the event that, at step 335, the calculated likelihood of infection does not exceed the one or more threshold levels, then the method loops back to step 325 so as to continue identifying and monitoring infection spread by applying the geospatial outbreak detection model to the database of spending records.

In the event that the calculated likelihood of infection exceeds the one or more threshold levels, then at step 340, the processor 110, which is configured by executing one or more of the software modules 130, including, preferably, the analysis module 172, and the reporting module 176 and the communication module 178, can generate an outbreak notification report.

In addition, the data exhibiting a likelihood of infection spread that exceeds the thresholds can also be provided as feedback to update and supplement the known indicators of infection, the probabilistic identification criteria as well as the geospatial outbreak detection model such that the system can more efficiently and accurately monitor infection spread based on the current state of the infection spread as identified by the system.

Figure 4:
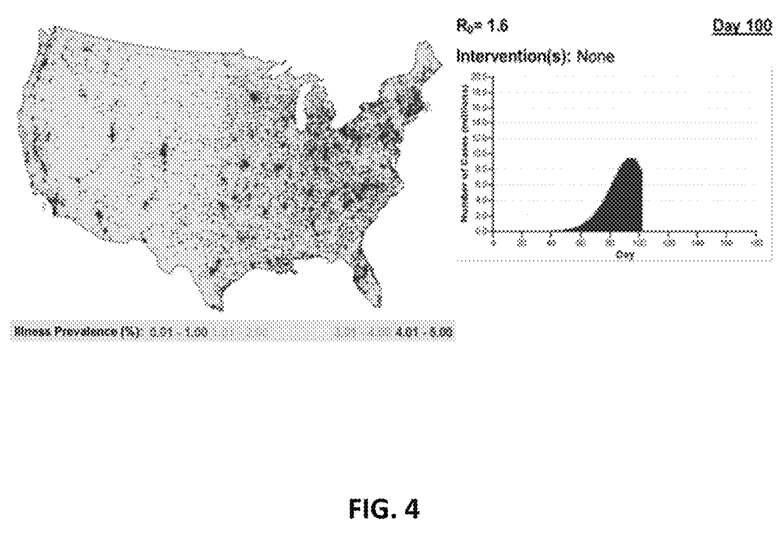
FIG. 4 is a screenshot of an exemplary report generated in accordance with at least one embodiment disclosed herein.

The outbreak notification report can provide individuals, or groups of individuals, medical providers, and authorities other regulatory entities information relating to the infection. For example, the report can notify a specific individual that they are likely to be infected, are at risk for infection (because they are part of a population or set at high risk) or otherwise provide general information concerning the outbreak and the at least one disease. Reports can also be transmitted to the individuals in a set or population exhibiting signs of infection by the at least one disease, for example, to provide a warning, information about the at least one disease and urge testing. Reports can also be transmitted to medical care providers or regulatory bodies to inform these entities as to the status of the outbreak and provide relevant information. A screenshot for an exemplary report detailing illness prevalence across the United States is show in FIG. 4.

The report can be printed and provided in paper form, for example to a known address of the appropriate individuals and entities. Alternatively or in addition, the report can be transmitted in an electronic format over the internet. The outbreak notification report can be transmitted by the configured processor 110 to individuals at respective remote individual devices 101. In addition or alternatively, the report can be transmitted to medical care providers or regulatory bodies at respective remote entity devices 102.

In addition, the configured processor 110, which is configured by executing one or more of software modules 130, including, preferably, the reporting module 176, can automatically generate recommendations for individuals and entities as a function of the geospatial outbreak detection model in view of the spending records. For example, if certain locations were identified as high risk, the report can identify those high risk locations to avoid and be transmitted to the individuals in that and surrounding areas about nearby locations that are high risk areas.

In addition, in certain embodiments, for example when alerts are generated or the calculated likelihood of infection exceeds certain levels or infected individuals are performing transactions, the system can cause actions to be taken at one or more remote computing devices, for example, remote computing device 192 shown in FIG. 2.

It can be appreciated that remote computing device 192 can be configured to coordinate electronic communication over a network between the system server 105 and/or other remote devices (e.g., individual device 101) and stand-alone computers, devices or servers (e.g., entity device 102) and coordinate action across the various remote devices. In some implementations, the remote devices can be transaction processing systems or related devices such as point of sale (POS) terminals. It can also be appreciated that the features and functionality of the remote computing device 192 can be distributed across one or more computing devices, such as the system server 105 and/or mobile devices (e.g., the individual device 101, the entity device 102, POS terminals, and the like). As shown in FIG. 2, the remote computing device 192 preferably includes one or more processors that are configured by executing one or more software modules, including an action processing module 195 that executes so as to configure the remote computing device 192 to perform certain actions in response to transmissions received from the system server 105 over a network.

In some implementations, the system server processor 110, which is configured by executing one or more of software modules 130, including, preferably, the reporting module 176, can transmit an alert over a network to the remote computing device 192, and causing at least one action to be taken at the remote computing device 192 in response to the transmission. In response to receipt of an alert or information relating to infection by one or more individuals conducting one or more purchases from the system server 105, the remote computing device 192, which is configured by executing the action processing module 195, can cause various actions to occur at the remote devices.

In some implementations, the configured remote computing device 192, can cause a telephone call to be placed to a particular individual's mobile device or transmit a message or e-mail to the particular individual or alert the authorities. In this manner, the computing device can also generate and transmit reports as described above.

In some implementations, the configured remote computing device 192 can be configured to elicit an action from the recipients of the messages. For example, the remote computing device 192 can present a message to the particular individual and prompt that individual to take a certain action, like call the CDC, or confirm receipt of the message or input additional information.

By way of further example, the remote computing device 192 can cause actions to occur at remote computing devices, for example, the remote computing device 192 can cause a point of sale terminal to notify an individual conducting a purchase of an elevated risk of infection at that location or inform the individual of a high likelihood of infection and prompt the user to contact authorities. In addition the remote computing device 192 can cause a remote transaction processing system or POS terminal to decline or delay a purchase being conducted by an individual, for example, if the terminal or the particular purchase transaction represents a high risk factor for infection, or if the individual is determined to have a high likelihood of infection or is known to be infected and the like. In addition the remote computing device 192 can cause the terminal to decline or hold a transaction being conducted by an individual pending an action by the individual at that terminal or another device. For example, the transaction can be delayed pending the individual responding to a message transmitted to their mobile device, or pending the user indicating receipt of a message provided via the terminal.

Accordingly it can be appreciated that the system 100, which includes the system server 105 in conjunction with the remote computing device 192 and remote devices distributed across a network, is configured to analyze and detect disease spread based on payment records that are updated in near-real time, proactively warn the population and authorities in an efficient and effective manner and aid in the efficient prevention of disease via the distributed network of computing devices.

At this juncture, it should be noted that although much of the foregoing description has been directed to systems and methods for conducting real-time active surveillance of disease, the systems and methods disclosed herein can be similarly deployed and/or implemented in scenarios, situations, and settings far beyond the referenced scenarios.

It should be appreciated that more or fewer operations can be performed than shown in the figures and described. These operations can also be performed in a different order than those described. It is to be understood that like numerals in the drawings represent like elements through the several figures, and that not all components and/or steps described and illustrated with reference to the figures are required for all embodiments or arrangements.

Thus, illustrative embodiments and arrangements of the present systems and methods provide a computer implemented method, computer system, and computer program product for real-time active surveillance of disease outbreak. The flowchart and block diagrams in the figures illustrate the architecture, functionality, and operation of possible implementations of systems, methods and computer program products according to various embodiments and arrangements. In this regard, each block in the flowchart or block diagrams can represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present disclosure, which is set forth in the following claims.

What is claimed is:

1. A computer-implemented method for real-time active surveillance of disease outbreak in a population of individuals from a database of spending records, wherein the spending records include SKU-level data, including temporal data and geographic data, concerning purchases conducted by the individuals in the population, and wherein the database of spending records is updated in real time as the individuals conduct additional purchases, the method comprising:

accessing from the database, using a processor configured by instructions in the form of code executing therein, respective spending records for individuals from among the population who are known to be infected by at least one disease ("infected individuals");

identifying, by the configured processor from the respective spending records, purchases made by the infected individuals that are indicative of infection in the population with the at least one disease, wherein the step of identifying purchases that are indicative of infection in the population includes:

analyzing, by the configured processor, the respective spending records, correlating, by the configured processor, the respective purchases with indicia of infection associated with the at least one disease based on at least one of: the temporal data and the geographic data and the purchase data concerning the respective purchases, and determining, by the configured processor, probabilistic identification criteria based on the correlation of the respective purchases with the indicia of infection;

generating, by the configured processor, a geospatial outbreak detection model that is a function of the probabilistic identification criteria and at least one simulation model of infection spread by geography, wherein the geospatial outbreak detection model is generated by seeding the at least one simulation model using the geographic data and temporal data included in the respective spending records for the infected individuals and wherein the seeded at least one simulation model identifies one or more geographic areas that are likely to exhibit infection spread based on a current state of the disease outbreak;

applying the geospatial outbreak detection model to the database of spending records, in near real-time, to identify one or more other purchases conducted in the one or more geographic areas that are likely to exhibit infection spread and that are indicative of infection in the population, wherein the one or more other purchases are conducted by one or more other individuals from among the population who are not known to be infected by the at least one disease ("candidate individuals");

calculating, by the configured processor, a likelihood that one or more of the candidate individuals are infected based on the one or more other purchases and the probabilistic identification criteria;

generating an alert if the calculated likelihood exceeds a threshold likelihood; and transmitting, by the configured processor, the generated alert over a network to a remote computing device being used by a particular candidate individual conducting a transaction, wherein the alert is configured to cause at least one action to be taken by the particular candidate individual at the remote computing device in response to the transmission; and interceding in the completion of the transaction pending receipt, by the configured processor, of an indication that the least one action was taken by the particular candidate individual at the remote computing device in response to the alert, wherein interceding includes one or more of delaying, holding or declining the transaction.

2. The method of claim 1, wherein the remote computing device is associated with the one or more of the candidate individuals conducting the one or more other purchases; and further comprising:

transmitting the generated alert, by the configured processor, over a network to a remote computing device associated with a regulatory agency.

3. The method of claim 1, wherein the remote computing device is a point of sale terminal used by the particular candidate individual to conduct the transaction.

4. The method of claim 3, wherein the alert includes a message to the particular candidate individual and is configured to intercede in the completion of the transaction by causing the remote computing device to prevent the particular candidate individual from conducting the transaction pending the particular candidate individual indicating receipt of the message.

5. The method of claim 1, wherein the step of identifying purchases that are indicative of infection in the population with the at least one disease further comprises:
identifying, by the configured processor, similarities between the respective purchases of two or more of the infected individuals by comparing the respective spending records based on at least one of: the SKU-level data, the temporal data and the geographic data;
identifying, by the configured processor, purchasing patterns based on the identified similarities; and
wherein the correlating step includes correlating the identified purchasing patterns with the indicia of infection.

6. The method of claim 5, further comprising updating the indicia of infection based on the identified patterns and a degree of correlation between the identified patterns and one or more of the indicia of infection.

7. The method of claim 5, wherein the identified purchasing patterns include individual level purchasing patterns and group level purchasing patterns.

8. The method of claim 1, wherein the indicia of infection identify at least one of:
products that are associated with individuals in the population who are known to be infected by the at least one disease;
merchants that are associated with individuals in the population who are known to be infected by the at least one disease;
locations that are associated with individuals in the population who are known to be infected by the at least one disease;
temporal windows that are associated with individuals in the population who are known to be infected by the at least one disease;
purchasing patterns that are associated with individuals in the population who are known to be infected by the at least one disease;
demographic characteristics that are associated with individuals in the population who are known to be infected by the at least one disease; and
environmental characteristics that are associated with individuals in the population who are known to be infected by the at least one disease.

9. The method of claim 1, wherein the probabilistic identification criteria are weighted according to a degree of correlation between the respective purchases and one or more of the indicia of infection.

10. The method of claim 1, wherein the probabilistic identification criteria are weighted according a respective risk factor associated with the indicia of infection.

11. The method of claim 1, wherein the purchase data identifies one or more of: a product; a service; and a merchant.

12. The method of claim 1, further comprising: obtaining a permission from each of the infected individuals and the candidate individuals to access the respective spending records.

13. The method of claim 1, further comprising:
identifying the plurality of infected individuals, using the configured processor, wherein the identifying step comprises:
retrieving, using the configured processor from a database of medical data, a particular consumers' medical data;
analyzing, using the configured processor, the particular consumers' medical data to determine that the particular consumer is infected by the at least one disease.

14. The method of claim 1, further comprising: anonymizing the spending records such that the individuals in the population are not personally identifiable from the spending records.

15. The method of claim 1, wherein each of the spending records are a transaction history from the use of a credit card, a debit card, a prepaid card, a gift card, bank account billpay service or ACH payment or a combination of the foregoing.

16. A system for real-time active surveillance of disease outbreak in a population of individuals from a database of spending records, wherein the spending records include purchase data, temporal data and geographic data concerning purchases conducted by the individuals in the population, and wherein the database of spending records is updated in real time as the individuals conduct additional purchases, comprising:
a non-transitory computer-readable storage medium;
a processor configured by executing one or more software modules including instructions in the form of code stored in the storage medium, the modules including:
a database module, that configures the processor to access, from the database, respective spending records for each of a plurality of individuals from among the population who were previously identified as being infected by at least one disease ("infected individuals");
an analysis module, that configures the processor to:
identify from the respective spending records, purchases that are indicative of infection in the population with the at least one disease by analyzing the respective spending records, and correlating the respective purchases with indicia of infection associated with the at least one disease based on at least one of: the purchase data, the temporal data and the geographic data concerning the respective purchases, and
determine probabilistic identification criteria based on the correlation of the respective purchases with the indicia of infection;
a modeling module that configures the processor to generate a geospatial outbreak detection model that is a function of the probabilistic identification criteria and at least one simulation model of infection spread by geography, wherein the geospatial outbreak detection model is generated by seeding the at least one simulation model using the geographic data and temporal data included in the respective spending records for the infected individuals and wherein the seeded at least one simulation model identifies one or more geographic areas that are likely to exhibit infection spread based on a current state of the disease outbreak;
wherein the analysis module further configures the processor to:
apply the geospatial outbreak detection model to the database of spending records, in real-time, to identify one or more other purchases conducted in the one or more geographic areas that are likely to exhibit infection spread and that are indicative of infection in the population, wherein the one or more other purchases are conducted by one or more other individuals from among the population who are not known to be infected by the at least one disease ("candidate individuals"), and calculate a likelihood that one or more of the candidate individuals are infected based on the one or more other purchases and the probabilistic identification criteria; and a reporting module that configures the processor to generate an alert if the calculated likelihood exceeds a threshold likelihood and transmit the generated alert over a network to a remote computing device being used by a particular candidate individual conducting a transaction, wherein the alert is configured to cause at least one action to be taken by the particular candidate individual at the remote computing device in response to the transmission; and an action processing module that configures the processor to intercede in the completion of the transaction pending receipt of confirmation that the least one action was taken by the particular candidate individual at the remote computing device in response to the alert, wherein the processor intercedes by one or more of delaying, holding or declining the transaction.

17. The system of claim 16, wherein the analysis module configures the processor to:

identify purchases that are indicative of infection in the population with the at least one disease by identifying similarities between the respective purchases of two or more of the infected individuals by comparing the respective spending records based on at least one of: the purchase data, the temporal data and the geographic data and, based on the identified similarities, identifying purchasing patterns; and wherein correlating the respective purchases with indicia of infection includes correlating the identified purchasing patterns with the indicia of infection.

18. The system of claim 17, wherein the analysis module configures the processor to update the indicia of infection based on the identified patterns and a degree of correlation between the identified patterns and one or more of the indicia of infection.

19. The system of claim 17, wherein the identified purchasing patterns include individual level purchasing patterns and set level purchasing patterns.

20. The system of claim 16, wherein the indicia of infection identify at least one of:

products that are associated with the at least one disease;
merchants that are associated with the at least one disease;
locations that are associated with the at least one disease;
temporal windows that are associated with the at least one disease;
purchasing patterns that are associated with the at least one disease;
demographic characteristics that are associated with the at least one disease; and
environmental characteristics that are associated with the at least one disease.

21. The system of claim 16, wherein the purchase data identifies one or more of: a product; a service; and a merchant.

* * * * *